(12) United States Patent
Ogawa et al.

(10) Patent No.: US 9,207,189 B2
(45) Date of Patent: Dec. 8, 2015

(54) SAMPLE SUPPORT APPARATUS

(71) Applicant: NuFlare Technology, Inc., Yokohama (JP)

(72) Inventors: Riki Ogawa, Kanagawa (JP); Hiromu Inoue, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 0 days.

(21) Appl. No.: 14/185,333

(22) Filed: Feb. 20, 2014

(65) Prior Publication Data

US 2014/0240700 A1    Aug. 28, 2014

(30) Foreign Application Priority Data

Feb. 28, 2013  (JP) .................................. 2013-39637
Dec. 9, 2013   (JP) ................................ 2013-254300

(51) Int. Cl.
*G01N 21/01* (2006.01)
*G01N 21/956* (2006.01)

(52) U.S. Cl.
CPC .............. *G01N 21/956* (2013.01); *G01N 21/01* (2013.01)

(58) Field of Classification Search
CPC .............................. G01N 21/01; G01N 21/956
USPC .................................................. 356/244, 601
See application file for complete search history.

(56) References Cited

U.S. PATENT DOCUMENTS

| 2010/0214561 | A1* | 8/2010 | Chikamatsu | ........ | G01N 21/9501 356/237.5 |
| 2014/0002826 | A1* | 1/2014 | Inoue | .................... | G01N 21/956 356/601 |
| 2014/0111636 | A1* | 4/2014 | Inoue et al. | ....................... | 348/92 |

FOREIGN PATENT DOCUMENTS

| JP | 2003-125411 | 4/2003 |
| JP | 2003-294420 | 10/2003 |
| JP | 2007-294930 | 11/2007 |
| JP | 2008-112178 | 5/2008 |
| JP | 2012-78164 | 4/2012 |
| JP | 2012-182467 | 9/2012 |
| KR | 10-2006-0093303 A | 8/2006 |

OTHER PUBLICATIONS

U.S. Appl. No. 14/059,847, filed Oct. 22, 2013, Hiromu Inoue, et al.
Office Action issued Mar. 23, 2015 in Korean Patent Application No. 10-2014-0022591 filed Feb. 26, 2014 (with English translation).

* cited by examiner

*Primary Examiner* — Roy M Punnoose
(74) *Attorney, Agent, or Firm* — Oblon, McClelland, Maier & Neustadt, L.L.P.

(57) ABSTRACT

A sample support apparatus is provided in which a XY-table and a Z-table moving along a height direction are disposed in a Z-reference surface as a height reference, and in which a sample is disposed at a predetermined height position while supported by the Z-table, the sample support apparatus comprising, a height correction unit that controls movement of the Z-table, and a Z-sensor that is provided on the Z-reference surface to measure the height from the Z-reference surface, wherein a measuring surface is aligned along the same axis with respect to a measuring position of the sample, the height of the measuring surface from the Z-reference surface is measured by the Z-sensor, the height correction unit moves the Z-table according to the measured value of the height so that the sample is disposed at the predetermined height position.

10 Claims, 11 Drawing Sheets

SAMPLE SUPPORT APPARATUS

CROSS-REFERENCE TO THE RELATED APPLICATION

The entire disclosure of Japanese Patent Application No. 2013-39637, filed on Feb. 28, 2013, and 2013-254300 filed on Dec. 9, 2013, including specifications, claims, drawings, and summaries, on which the Convention priority of the present application is based, are incorporated herein in their entirety.

FIELD OF THE INVENTION

The present invention relates to a Sample Support Apparatus.

BACKGROUND

With high integration and large capacity of a Large Scale Integration (LSI), a circuit dimension required for a semiconductor element becomes increasingly narrow. Using an original image pattern (that is, a mask or a reticle, hereinafter collectively referred to as a mask), a reduced-projection exposure apparatus called a stepper or a scanner exposes and transfers the pattern on a wafer to form a circuit, thereby producing the semiconductor element.

It is necessary to improve a production yield for costly LSI production. Furthermore, there is a demand for pattern formation having a line width of 10 nanometers in a contemporary typical logic device. At this point, a shape defect of the mask pattern and a deviation of various process conditions when the pattern is exposed and transferred on a wafer can be cited as a large factor that degrades the production yield. With a fine LSI pattern on the semiconductor wafer, the shape defect of the mask pattern becomes finer. Because dimensional accuracy of the mask is enhanced in order to absorb deviations of various process conditions, it is necessary to detect a defect of the extremely small pattern in the mask inspection. Therefore, high accuracy for inspection is required for an inspection apparatus that inspects the linewidth of a transfer mask used in LSI production.

There is a known inspection apparatus that inspects an inspection target mask by capturing an optical image of a pattern of the mask using an image sensor. In this inspection apparatus, the inspection target mask is irradiated with light emitted from a light source through an optical system. The mask is supported on a table and scanned with the emitted light by movement of the table. An image of the light transmitted through or reflected by the mask is formed on the image sensor through a lens, and the optical image captured by the image sensor is transmitted as measurement data to a comparison unit. In the comparison unit, the measurement data and reference data are compared to each other according to a predetermined inspection algorithm. A determination that a defect exists is made unless the measurement data matches the reference data (see for example, JP 2008-112178).

With the progress of microfabrication of the pattern formed on the mask, high magnification and high NA (Numerical Aperture) are being developed in an inspection optical system that captures the optical image of the pattern. Therefore, a focal depth that is of a permissible range of a distance between the optical system and the mask is deepened, focusing cannot be performed even by changing the distance between the optical system and the mask slightly, and the pattern image becomes blurred, which causes a problem in defect detection processing. For this reason, an auto focus unit that can maintain a focused state so as to always keep the distance between the optical system and the mask constant is used.

JP 2003-294420 discloses an auto focus unit that adjusts a focal position of an inspection optical system to a surface of the mask. In the auto focus unit, when the mask is irradiated with light from the light source, the light reflected by the mask is incident to an optical sensor. An electric signal of the incident light is digitally converted, and input to a height measurement circuit. The height measurement circuit outputs a difference signal between an input offset value and a target height. The difference signal is input to a Z-table driving circuit that drives a Z-table in a Z-direction (height direction). The Z-table driving circuit drives the Z-table in response to the difference signal. Therefore, the distance between the optical system and the mask can be kept constant to maintain the focused state.

In recent years, the pattern of the inspection target mask has become finer than before, and frequently a line width or a pitch of the pattern becomes less than or equal to a wavelength of the light used in the optical system of the inspection apparatus. When the line width or pitch of the pattern becomes less than or equal to the wavelength of the light used in the optical system for defect detection, diffracted light is generated in the pattern, and sometimes the focus position cannot correctly be detected. Particularly, in the case that the line width of the pattern of the inspection target mask becomes less than or equal to an optical resolution limit, since the pattern is not resolved, sometimes the focus cannot be put on the pattern. As a result, sometimes focus accuracy cannot be guaranteed in the sample inspection.

There is a known method, in which a focus measuring surface is provided in a predetermined place of the sample, the focus is put on the focus measuring surface, the focus is then put on the inspection position in the pattern of the mask based on the focus put on the focus measuring surface. However, during the inspection, a mechanical displacement of a position (Z-position) in a Z-direction (height direction), gravitational distortion of the sample, and a focus displacement caused by a change in temperature or atmospheric pressure are generated when the sample is moved in an X-direction or a Y-direction (horizontal direction). The mechanical displacement, the gravitational distortion of the sample, and the focus displacement have an influence on the inspection. Therefore, in using only the focus-measuring surface provided in the sample, sometimes the focus accuracy cannot be guaranteed in the actual inspection of the sample.

The present invention has been devised to solve the above problems. Considering the above, an object of the present invention is to provide a sample support apparatus that can accurately adjust the height (Z) position of the sample to the target position so as to be able to inspect the inspection position of the sample with high focus accuracy.

Other challenges and advantages of the present invention are apparent from the following description.

SUMMARY OF THE INVENTION

According to one aspect of the present invention, a sample support apparatus in which a XY-table and a Z-table moving along a height direction are disposed in a Z-reference surface as a height reference, and in which a sample is disposed at a predetermined height position while supported by the Z-table, the sample support apparatus comprising, a height correction unit that controls movement of the Z-table; and a Z-sensor that is provided on the Z-reference surface to measure the height from the Z-reference surface, wherein a measuring surface is aligned along the same axis with respect to a measuring position of the sample, the height of the measuring surface from the Z-reference surface is measured by the Z-sensor, the height correction unit moves the Z-table according to the measured value of the height so that the sample is disposed at the predetermined height position.

Further to this aspect of the present invention, the sample support apparatus, wherein the measuring surface aligned along the same axis with respect to the measuring position of the sample includes a first measuring surface and a second measuring surface, the measuring position of the sample being interposed between the first measuring surface and the second measuring surface, the Z-sensor includes a first Z-sensor and a second Z-sensor, the first Z-sensor and the second Z-sensor being provided on the Z-reference surface, the height of the first measuring surface from the Z-reference surface is measured by the first Z-sensor, the height of the second measuring surface is measured by the second Z-sensor, the height correction unit moves the Z-table according to each measured value of the height so that the sample is disposed at the predetermined height position.

Further to this aspect of the present invention, the sample support apparatus, wherein the Z-table supports the sample at three points, the Z-table includes a measurement unit that sequentially irradiates at least four reference positions separated from one another on a measured sample surface with light, receives reflected light to sequentially measure the heights of at least the four reference positions, and produces a Z-map indicating a height distribution of the sample surface, the height correction unit moves the Z-table according to the measured value of the height by the Z-sensor and according to the Z-map by the measurement unit so that the sample is disposed at the predetermined height position.

Further to this aspect of the present invention, the sample support apparatus, wherein the height correction unit corrects the Z-map in consideration of gravitational distortion of the sample and a displacement in a height direction of the Z-table so that the sample is disposed at the predetermined height position.

Further to this aspect of the present invention, the sample support apparatus, wherein the measurement unit includes a lens that sequentially focuses the light, a holding unit that holds the lens, and a base that is disposed on the Z-reference surface to position the Z-sensor thereon, and the height correction unit corrects the Z-map according to a displacement in focal position of the lens due to an influence of thermal expansion of the holding unit and a displacement in position of the Z-sensor due to the thermal expansion of the base so that the sample is disposed at the predetermined height position.

Further to this aspect of the present invention, the sample support apparatus, wherein the measurement unit includes a lens that sequentially focuses the light, a holding unit that holds the lens, and a base that is disposed on the Z-reference surface to position the Z-sensor thereon, and the height correction unit corrects the Z-map according to a displacement in focal position of the lens due to an influence of thermal expansion of the holding unit and a displacement in installation position of the Z-sensor due to the thermal expansion of the base so that the sample is disposed at the predetermined height position.

Further to this aspect of the present invention, the sample support apparatus, wherein the height correction unit corrects the Z-map according to a displacement in focal position of the lens due to the influence of a change in refractive index of air caused by a change in atmospheric pressure so that the sample is disposed at the predetermined height position.

Further to this aspect of the present invention, the sample support apparatus, wherein the height correction unit corrects the Z-map according to a displacement in focal position of the lens due to the influence of a change in refractive index of air caused by a change in atmospheric pressure so that the sample is disposed at the predetermined height position.

Further to this aspect of the present invention, the sample support apparatus, wherein the height correction unit corrects the Z-map according to a displacement in focal position of the lens due to the influence of a change in refractive index of air caused by a change in atmospheric pressure so that the sample is disposed at the predetermined height position.

Further to this aspect of the present invention, the sample support apparatus, wherein the Z-sensor is at least one of an electrostatic capacitance sensor, an electromagnetic induction sensor, and an optical sensor.

DETAILED DESCRIPTION OF THE EMBODIMENT

Figure 1:
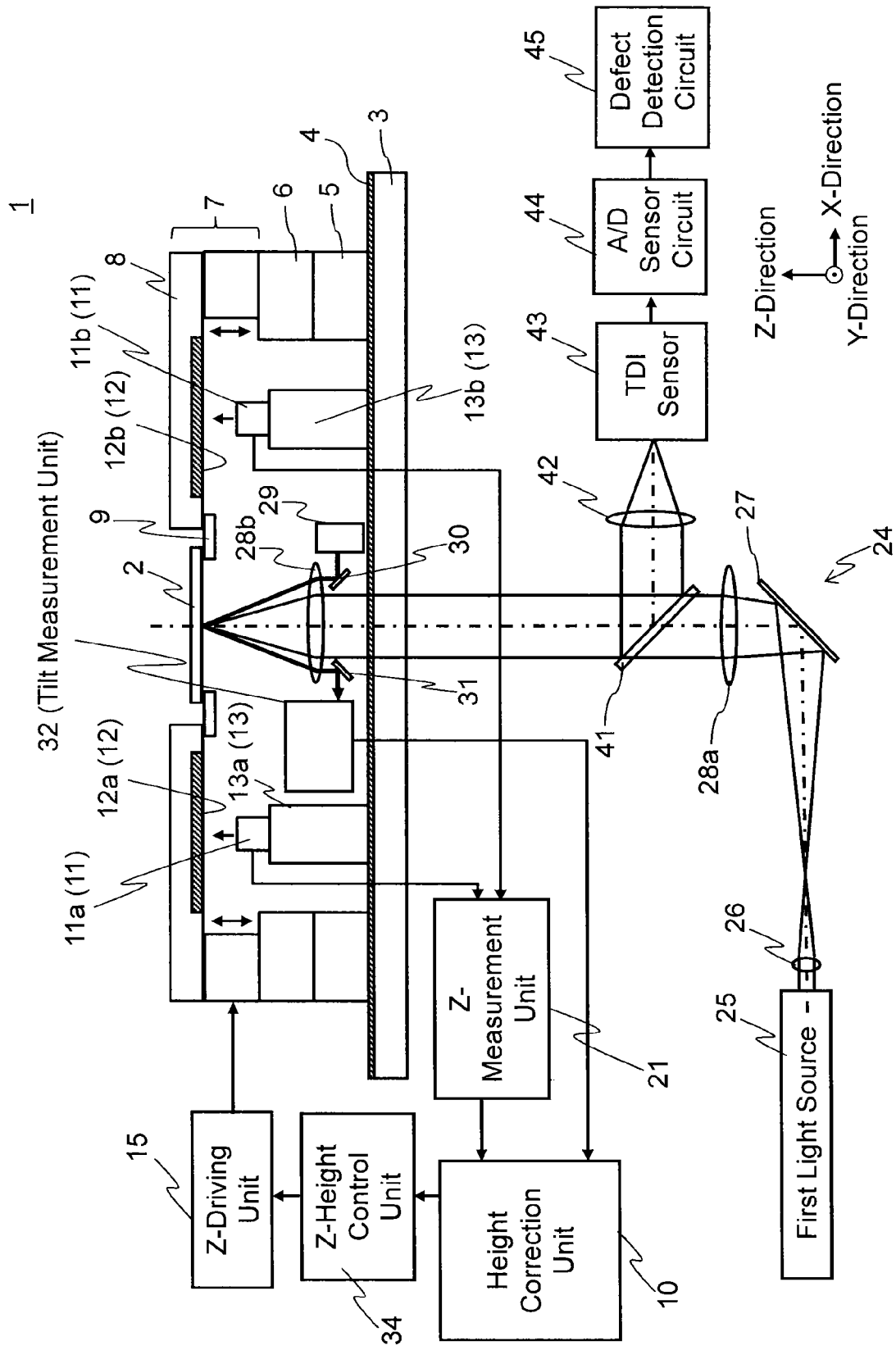
FIG. 1 is a view illustrating a configuration of a sample support apparatus according to an embodiment of the present invention.

FIG. 1 is a view illustrating a configuration of a sample support apparatus according to the embodiment of the present invention.

A sample support apparatus 1 of the embodiment of the present invention in FIG. 1 is one that adjusts a sample position, and the sample support apparatus 1 can be used while incorporated in an inspection apparatus (not illustrated) that performs inspection by optically magnifying an optical image of a sample 2 of an inspection target. The sample support apparatus 1 can accurately adjust a height (Z) position of the sample 2 to a desired position such that the inspection apparatus can inspect an inspection position of the sample 2 with high focus accuracy.

The sample support apparatus 1 in FIG. 1 includes a flat base 3. An upper surface of the base 3 constitutes a Z-reference surface 4 that is a height reference of the sample support apparatus 1. In FIG. 1, for the sake of convenience, the Z-reference surface 4 is illustrated as a part of the base 3 having a thickness. However, the Z-reference surface 4 is only a specific surface of the base 3 and is not an individual component.

A Y-table 5 and an X-table 6 are sequentially disposed on the Z-reference surface 4 that is the height reference of the sample support apparatus 1 in the base 3, and a Z-table 7 is disposed on the X-table 6. The Z-table 7 is configured to be vertically (perpendicularly) movable along the height (Z) direction, and the Y-table 5 and the X-table 6 are movable in the horizontal direction.

As illustrated in FIG. 1, the Z-table 7 includes a sample support 8 on the top thereof, a support body 9 is provided in the sample support 8 such that the sample 2 can be supported.

Figure 2:
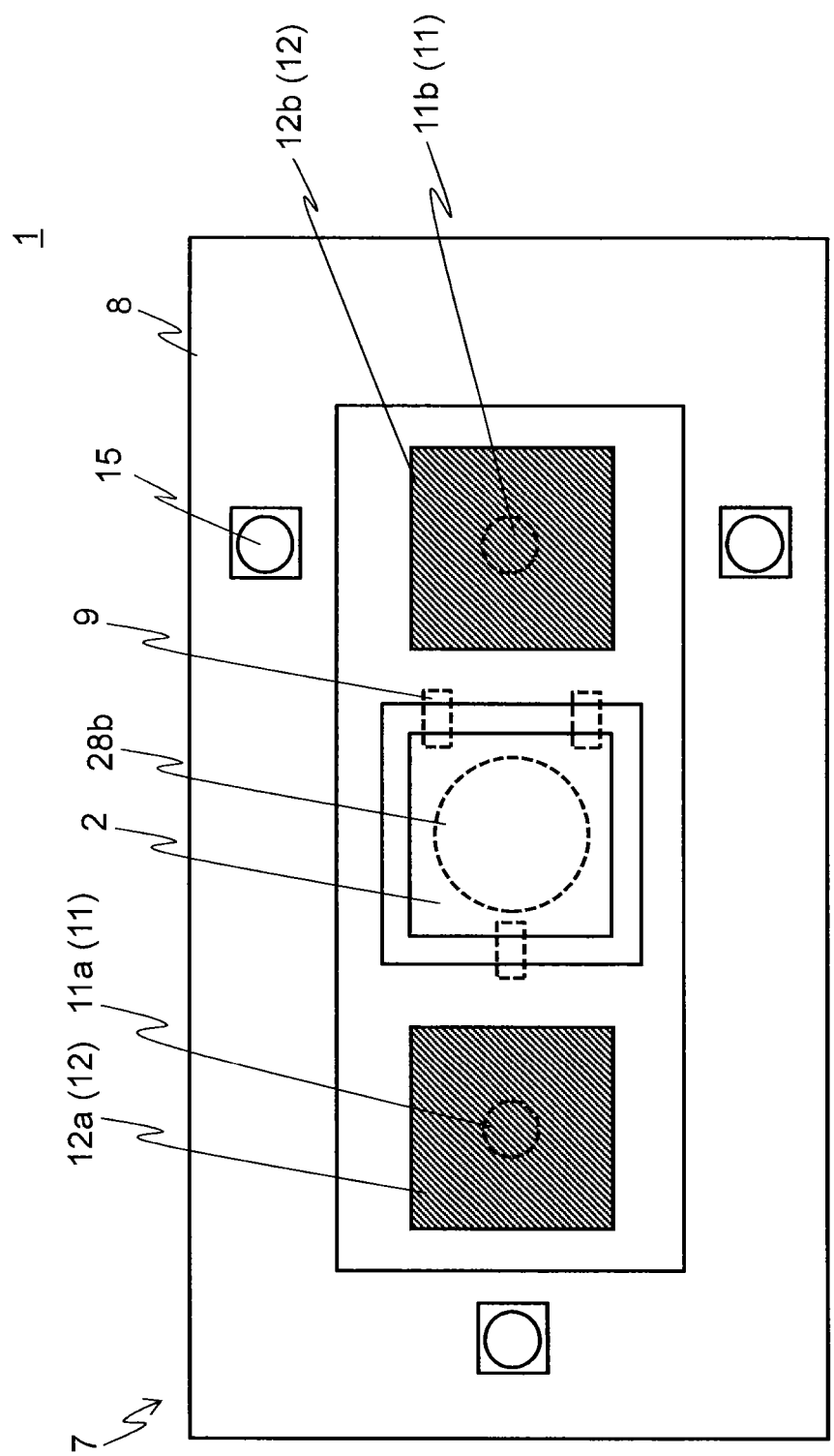
FIG. 2 is a schematic plan view of the sample support apparatus of the embodiment of the present invention.

FIG. 2 is a schematic plan view of the sample support apparatus of the embodiment of the present invention.

As illustrated in FIGS. 1 and 2, the sample support 8 of the Z-table 7 has a flat plate shape in which an opening constituting a hollow portion is provided near a center. The opening may be provided as a notch portion that is formed by notching aside in a lengthwise direction of the sample support 8. In the sample support 8, the three support bodies 9 are disposed around the opening, and the sample 2 can be supported from below by three-point supporting method using the three support bodies 9.

For example, the support body 9 is constructed by a ball point in which a head surface touching the sample 2 is formed into a spherical shape. Two of the three support bodies 9 are in contact with the sample 2 at two adjacent corners that are not diagonal in four corners of the sample 2. The remaining one support body from the three support bodies 9 is disposed in a region between the two corners where the two support bodies 9 are not disposed.

At this point, for example, the sample 2 is a plate shape. The sample 2 can have a mesa structure in which a central portion projects from an outer peripheral portion. A pattern (not illustrated) that becomes an inspection target of the sample 2 is formed on a rectangular mesa portion (also referred to as a land portion). A replica template used in a nano-imprint technology can be cited as an example of the sample 2. In this embodiment, the mesa portion in which the pattern is formed in the sample 2 is disposed downward so as to be oriented toward the side of the Z-reference surface 4 of the base 3 located in a lower portion of the sample support apparatus 1.

The sample support apparatus 1 of the embodiment can also be applied to the plate-shape sample 2 in which the inspection target pattern (not illustrated) is formed without providing the mesa portion.

It is conceivable that the Z-table 7 is configured to support the sample 2 at four points. However, in the case that the sample 2 is supported at the four points, it is necessary to accurately adjust a height with respect to the support body 9. Possibly the insufficient height adjustment deforms the sample 2. On the other hand, in the sample support apparatus 1, the Z-table 7 is configured to support the sample 2 at the three points as described above. The three-point supporting method can support the sample 2 while the deformation of the sample 2 is suppressed to the minimum.

As illustrated in FIG. 2, in the Z-table 7, three Z-driving units 15 are disposed so as to correspond to the dispositions of the support bodies 9 in the sample support 8. In the Z-table 7, the sample support 8 can vertically be moved along a height direction by the Z-driving units 15.

The three Z-driving units 15 of the Z-table 7 can independently be driven under control of a height correction unit 10 mentioned later, and a portion in which the Z-driving unit 15 is installed in the sample support 8 can vertically be moved. Accordingly, the height of the sample support 8 and therefore the height of the support body 9 are adjusted such that the sample 2 supported by the three support bodies 9 cannot deform whereby the height of the sample 2 is adjusted and the sample 2 can be tilted such that the pattern forming surface of the sample 2 is aligned with a horizontal surface.

The sample support apparatus 1 includes a height correction unit 10 and is capable of controlling motion of the Z-table 7.

Z-sensors 11 are provided on the Z-reference surface 4 in order to measure the height in the sample support apparatus 1, namely, the height from the Z-reference surface 4. In the sample support apparatus 1, measuring surfaces 12 are aligned along the same axis with respect to a measuring position that becomes the inspection position of the sample 2.

The measuring surface 12 of the sample support apparatus 1 is provided in the Z-table 7. More specifically, the two measuring surfaces 12 including a first measuring surface 12a and a second measuring surface 12b are provided in the surface opposed to the Z-reference surface 4 of the sample support 8 of the Z-table 7. The first measuring surface 12a and the second measuring surface 12b are aligned along the same axis with respect to the measuring position that becomes the inspection position of the sample 2 while the measuring position that becomes the inspection position of the sample 2 interposed therebetween. In FIG. 1, for the sake of convenience, the first measuring surface 12a and the second measuring surface 12b are illustrated as parts of the sample support 8 having a thickness. However, the first measuring surface 12a and the second measuring surface 12b are only surfaces not actually having a thickness.

Accordingly, the Z-sensor 11 includes the first Z-sensor 11a and the second Z-sensor 11b, which are provided above the Z-reference surface 4, so as to correspond to the dispositions of the first measuring surface 12a and second measuring surface 12b.

The first Z-sensor 11a and the second Z-sensor 11b are provided above the Z-reference surface 4 while supported on bases 13a and 13b having a known height, respectively. A distance between the Z-reference surface 4 and the first Z-sensor 11a and second Z-sensor 11b is measured. Height dimensions (dimensions in Z-height direction) of the first Z-sensor 11a, second Z-sensor 11b, and bases 13a and 13b are already known. Accordingly, using the height dimensions, or by measuring the height of the first measuring surface 12a from the Z-reference surface 4 with the first Z-sensor 11a, the height of the second measuring surface 12b can be measured with the second Z-sensor 11b.

Specifically, signals output from the first Z-sensor 11a and second Z-sensor 11b are converted from current values into voltage values by I/V conversion amplifier incorporated in a Z-measurement unit 21 connected to the first Z-sensor 11a and second Z-sensor 11b. The voltage values are amplified to appropriate voltage levels by a non-inverting amplifier, and converted into digital data by an A/D conversion unit, thereby producing height data related to each of the heights of the first measuring surface 12a and second measuring surface 12b.

In the sample support apparatus 1, at least one of an electrostatic capacitance sensor, an electromagnetic induction sensor, and an optical sensor can be used as the Z-sensor 11, namely, the first Z-sensor 11a and the second Z-sensor 11b. When the electrostatic capacitance sensor, the electromagnetic induction sensor, or the optical sensor is used as the Z-sensor 11, the sample support apparatus 1 can accurately measure the height of the measuring surface 12 from the Z-reference surface 4. That is, the heights of the first measuring surface 12a and second measuring surface 12b from the Z-reference surface 4 can accurately be measured in the sample support apparatus 1.

In FIG. 1, the height data produced by the Z-measurement unit 21 with respect to the first measuring surface 12a and second measuring surface 12b are transmitted to the height correction unit 10 connected to the Z-measurement unit 21, and used to control the motion of the Z-table 7.

In the sample support apparatus 1 in FIG. 1, an optical system 24 is disposed below the sample 2. The optical system 24 optically inspects the sample 2 when the inspection apparatus is constructed using the sample support apparatus 1. Some components of the optical system 24 can also be used to measure the height of the sample 2. In this case, using the optical system 24, the height (Z) position of the sample 2 can accurately be adjusted to the target position in the sample support apparatus 1, and the inspection position of the sample 2 can be inspected with high focus accuracy in the inspection apparatus provided with the sample support apparatus 1.

In the optical system 24, a first light source 25 irradiates the sample 2 with defect inspection light. The light emitted from the first light source 25 is transmitted through a lens 26, the direction of the light is changed by a mirror 27, and lenses 28a and 28b focus the light on the inspection position on the sample 2. The sample support apparatus 1 includes the lenses 26, 28a, and 28b and a holding unit (not illustrated) that holds the mirror 27, and these components are installed at predetermined positions.

A mirror 41, a lens 42, a TDI (Time Delay and Integration) sensor 43, an A/D circuit 44, and a defect detection circuit 45 are disposed below the sample 2, the light reflected downward by the sample 2 is focused on the TDI sensor 43 to form an image, and an optical image used in the inspection of the inspection apparatus is generated.

In the inspection apparatus, the optical image is transmitted as measurement data to a comparison unit of the inspection apparatus. In the comparison unit, the measurement data is compared to reference data according to an appropriate algorithm. Unless the measurement data matches the reference data, a determination of the existence of a defect is made as an inspection result.

In the optical system 24, a second light source 29 emits height measuring light to the sample 2. The direction of the light emitted from the second light source 29 is changed by a mirror 30, and the inspection position on the sample 2 is irradiated with the light. After being reflected on the sample 2, the light is incident to a tilt measurement unit 32 by a mirror 31. A light projection lens that causes the light emitted from the second light source 29 to converge on the sample 2 and a light receiving lens, which receives the light reflected on the sample 2 and causes the light to converge, are omitted in FIG. 1.

The tilt measurement unit 32 includes a light receiving element (not illustrated). For example, a Position Sensitive Detector (PSD) is used as the light receiving element. The PSD has the same structure as a PIN photodiode. In the PSD, a photocurrent is measured by a photovoltaic effect to perform measurement of a center of gravity of the received light.

In the tilt measurement unit 32, the signal output from the light receiving element is converted from the current value into the voltage value by the I/V conversion amplifier. The voltage value is amplified to the appropriate voltage level by the non-inverting amplifier, and converted into the digital data by the A/D conversion unit, thereby producing the height data of the surface of the sample 2 according to the position of the light detected by the light-receiving element.

A specific example of a height data producing method is cited below.

The light emitted from the second light source 29 converges on the surface of the sample 2 using the light projection lens. The converged light is reflected by the surface of the sample 2, is incident to the light receiving lens, and converges on the PSD of the tilt measurement unit 32. When spot light is incident to the PSD, a charge is generated at a light incident position in proportion to light energy, and the charge flows to electrodes placed at two end surfaces of the PSD through a resistant layer (P-layer) having an even resistance value. At this point, a current amount is divided in reverse proportion to the distance to the electrode. Assuming that I1 is an output current from the electrode placed at one of the end surfaces while I2 is an output current from the electrode placed at the other end surface, a center of gravity position X from the center of the spot light on the PSD can be obtained by the equation (1). Where L is a length of a light receiving surface. A total photocurrent indicating a light receiving intensity of the PSD is obtained by a sum of I1 and I2.

$$X = L/2 \times (I_1 - I_2)/(I_1 + I_2) \tag{1}$$

The center of gravity position of the incident light is obtained by measuring two amounts of weak current change. Therefore, usually an I/V conversion circuit is constructed to individually convert output current changes (I1 and I2) from the PSD into output voltage changes (V1 and V2) and the center of gravity position of the light is measured. At this point, since a dark current of the light receiving element, a leak current on the circuit, and an offset current of the I/V conversion amplifier exist as an error on the production, the sum of the dark current, the leak current, and the offset current acts on the output voltage as an offset voltage (V10 and V20) of the whole circuit. That is, assuming that V1 and V2 are the output voltages after the voltage conversion, the measured height Z is expressed by the equation (2). Where α is a coefficient that is decided from a sample height measuring range and a center of gravity moving range of the light on the PSD.

$$Z = \alpha \times (V_1 - V_2)/(V_1 + V_2) \tag{2}$$

However, an actually-measured height Z' is expressed by the equation (3) in consideration of the offset voltage. In the equation (3), V10 and V20 are the offset voltages.

$$Z' = \alpha \times \{(V_1 + V_{10}) - (V_2 + V_{20})\}/\{(V_1 + V_{10}) + (V_2 + V_{20})\} \tag{3}$$

The tilt measurement unit 32 includes a Z-map producing unit (not illustrated). Based on the height data, the Z-map producing unit of the tilt measurement unit 32 produces a Z-map (Z-height map). The Z-map indicates a height distribution expressing a tilt state and a twist or undulation state of the surface of the sample 2.

In the sample support apparatus 1 in FIG. 1, the second light source 29, the lens 28b, the mirrors 30 and 31, the light projection lens and light receiving lens (not illustrated), and the tilt measurement unit 32, which are constructional elements of the optical system 24, constitute a measurement unit that measures the height of the sample 2.

Figure 3:
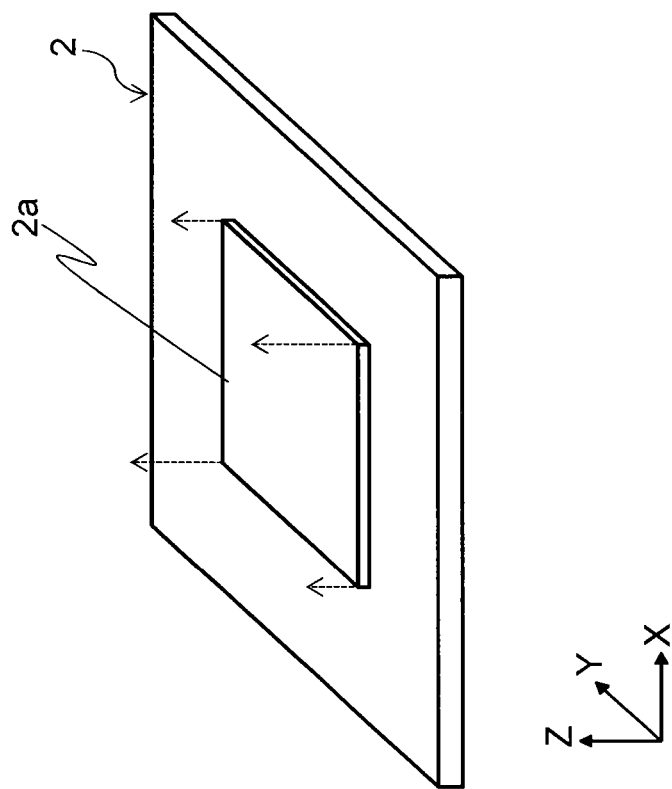
FIG. 3 is a perspective view schematically illustrating the sample.

FIG. 3 is a perspective view schematically illustrating the sample.

As described above, the sample 2 includes the mesa portion 2a in the surface thereof, and the mesa portion 2a becomes the inspection region of the sample 2. Four arrows located at four corners of the mesa portion 2a of the sample 2 express four reference positions separated from one another, the light from the second light source 29 is focused on each of the reference positions by the lens 28b, thereby obtaining a height measuring position at which the height is measured. A difference in length between the arrows reflects a difference in height data between the height measuring positions.

At this point, the height measuring position is not limited to the four corners as long as the height measuring position is set to a peripheral edge portion, and the number of measuring points is not limited to four. That is, the height measuring position is not limited to the four corners as long as the height measuring position is set to the peripheral edge portion, but at least four corners may be set to the height measuring position, and therefore the number of measuring points may be set to at least four. As a result, the inspection apparatus can properly deal with the height distribution of a more complicated surface of the sample 2.

Even if the sample 2 does not include the mesa portion 2a, the Z-map can be produced based on the peripheral edge of, for example, the four corners of the inspection region where the pattern is formed.

In the Z-map producing unit of the tilt measurement unit 32, the Z-map indicating the tilt state of the mesa portion 2a is produced by linearly interpolating the height data at the four corners of the mesa portion 2a that is of the inspection region produced in the tilt measurement unit 32. The height data is produced by the tilt measurement unit 32.

Figure 4:
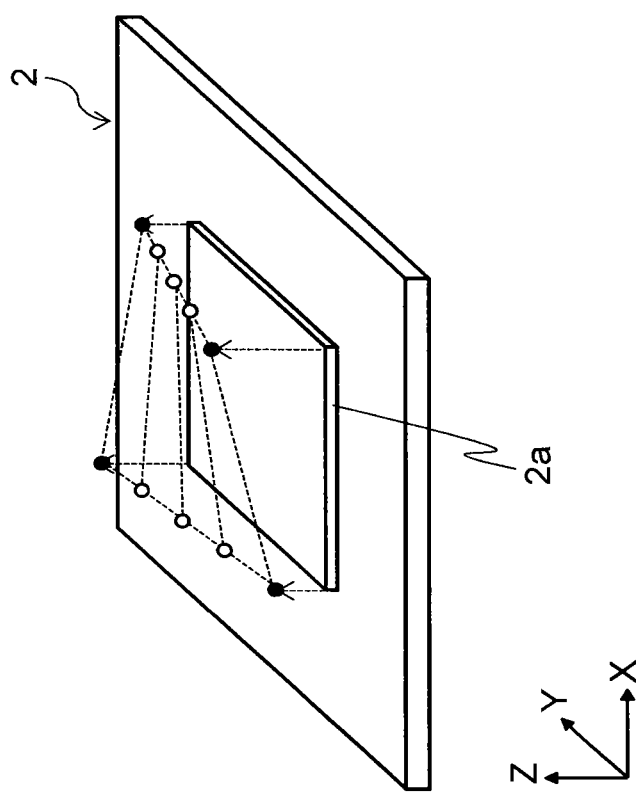
FIG. 4 is a view illustrating the Z-height map of the sample.

FIG. 4 is a view illustrating the Z-height map of the sample.

A black circle in FIG. 4 indicates the height data measured by the tilt measurement unit 32. A white circle in FIG. 4 indicates the height data that is obtained by the liner interpolation based on the measured value. The Z-map is a dotted line connecting the height data measured at the four corners and the height data obtained by the linear interpolation.

Referring to FIG. 1, Z-map data produced by the Z-map producing unit of the tilt measurement unit 32 is transmitted to the above-mentioned height correction unit 10 connected to the tilt measurement unit 32. Positional information on the Y-table 5 and X-table 6, which are measured by a laser interferometer (not illustrated), are also transmitted to the height correction unit 10.

The Z-map data is input to the height correction unit 10 from the Z-map producing unit of the tilt measurement unit 32 in FIG. 1. Even in the tilt state in which the pattern surface of the mesa portion 2a of the sample 2 is tilted in one direction with respect to the horizontal surface, or even in the twist state in which the pattern surface is twisted, the height is corrected using the Z-map, whereby the distance between the optical system 24 and the sample 2 can be adjusted so as to be kept constant.

The data of the height (Z-map target value) that becomes the inspection position target of the sample 2 is obtained from the XY-positional information on the Y-table 5 and X-table 6 using the Z-map, and the height data is transmitted to the Z-height control unit 34 connected to the height correction unit 10. The Z-height control unit 34 controls each Z-driving unit 15 of the Z-table 7 based on the height data from the height correction unit 10, and adjusts the height of the sample 2 to the target height.

As described above, the height data of the first measuring surface 12a and second measuring surface 12b, which are produced by the Z-measurement unit 21 in FIG. 1, are transmitted to the height correction unit 10.

At this point, in the case that the height of the measuring surface 12, namely, the height of the first measuring surface 12a and/or the height of the second measuring surface 12b deviates from a predetermined value in the sample support apparatus 1, the correction is simultaneously performed by the height correction unit 10. That is, the height correction unit 10 corrects the Z-map, thereby correcting the Z-map target value. As a result, based on the corrected height data from the height correction unit 10, the Z-height control unit 34 controls each Z-driving unit 15 of the Z-table 7 to adjust the height of the sample 2.

Therefore, even if the position (Z-position) in the Z-direction (height direction) of the sample 2 fluctuates when the sample 2 is moved in the X-direction or Y-direction (horizontal direction) during the inspection of the sample 2, the height (Z) position of the sample 2 can more accurately be adjusted to the target position, and the inspection position of the sample 2 can be inspected with high focus accuracy.

The correction of the Z-map target value is not limited to the height position of the measuring surface 12. For example, an influence of displacement in the Z-direction due to gravitational distortion of the sample 2 or the gravitational distortion of the sample support 8 of the Z-table 7 is considered desirable in correcting the Z-map target value. The unintentional displacement in the Z-direction such as the gravitational distortion of the Z-table 7, accuracy of the measuring surface 12, the tilt during the attaching process, and the displacement caused by a mechanical factor in moving the sample 2 in the X-direction or Y-direction (horizontal direction) is referred to as "the displacement in the Z-direction" or "the displacement in the height direction", and used in distinction from the intentional movement in the Z-direction by the Z-table of the sample 2.

Figure 5:
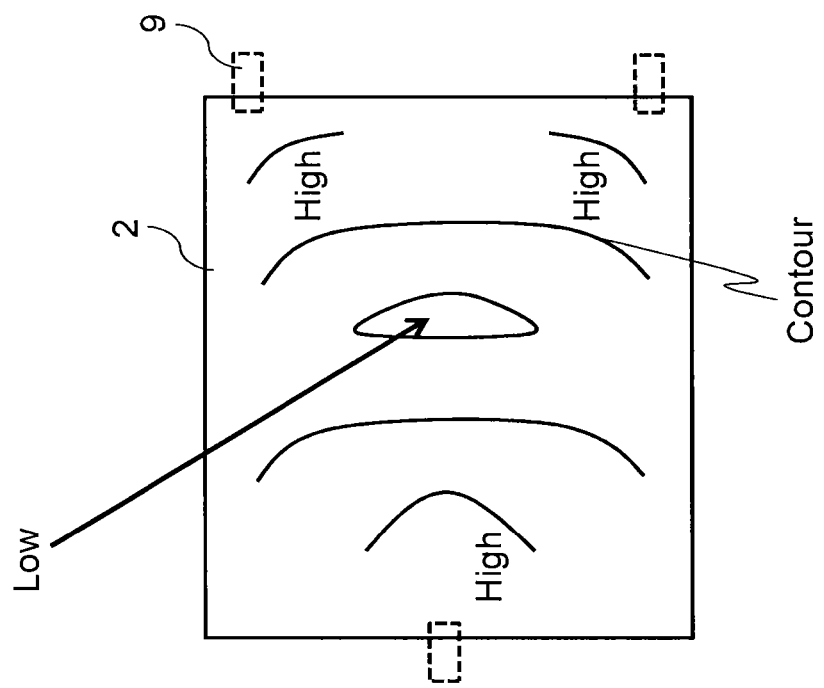
FIG. 5 is the view schematically illustrating the height (Z) displacement of the sample surface due to the gravitational distortion in the case that the sample is supported at three points.
Figure 6:
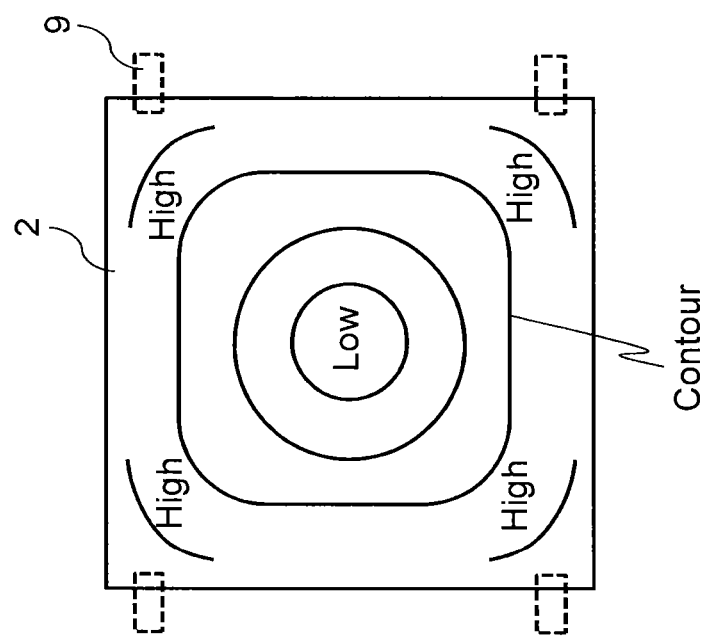
FIG. 6 is the view schematically illustrating the height (Z) displacement of the sample surface due to the gravitational distortion in the case that the sample is supported at four points.

FIGS. 5 and 6 are views schematically illustrating height displacement of the sample surface due to the gravitational distortion. FIG. 5 is a view schematically illustrating the height (Z) displacement of the sample surface due to the gravitational distortion in the case that the sample is supported at three points. FIG. 6 is a view schematically illustrating the height (Z) displacement of the sample surface due to the gravitational distortion in the case that the sample is supported at four points.

FIGS. 5 and 6 schematically illustrate a contour expressing the Z-height, and schematically illustrate a situation in which the sample 2 supported by the support bodies 9 distorts. As can be seen from FIGS. 5 and 6, the sample 2 supported by the support bodies 9 distorts such that the vicinity of the central portion is recessed downward (toward the side of the Z-reference surface 4).

The influence of the gravitational distortion of the sample 2, which is generated in the sample 2 by the three-point supporting method or four-point supporting method using the support bodies 9 as illustrated in FIGS. 5 and 6, namely, the height displacement of each portion can be calculated by a well-known structural calculation. In the four-point supporting method, sometimes it is difficult to equally support the sample 2 due to a shape variation in the Z-height direction of the sample 2 or a variation in height adjustment accuracy of the support body 9. Accordingly, in the three-point supporting method, the sample 2 can equally be supported by the support bodies 9 and the influence of the gravitational distortion on the sample 2 is accurately evaluated.

In the case that a variation in rigidity of the sample 2 exists due to individual differences of a sample 2, since a distortion amount varies, the Z-height is measured in the central portion of the actually supported sample 2, and used to correct the Z-map target value.

Thus, because the Z-map target value is previously corrected in consideration of the influence of the gravitational distortion, the accuracy of the Z-position can significantly be improved, and the inspection position of the sample 2 can be inspected with high focus accuracy.

Figure 7:
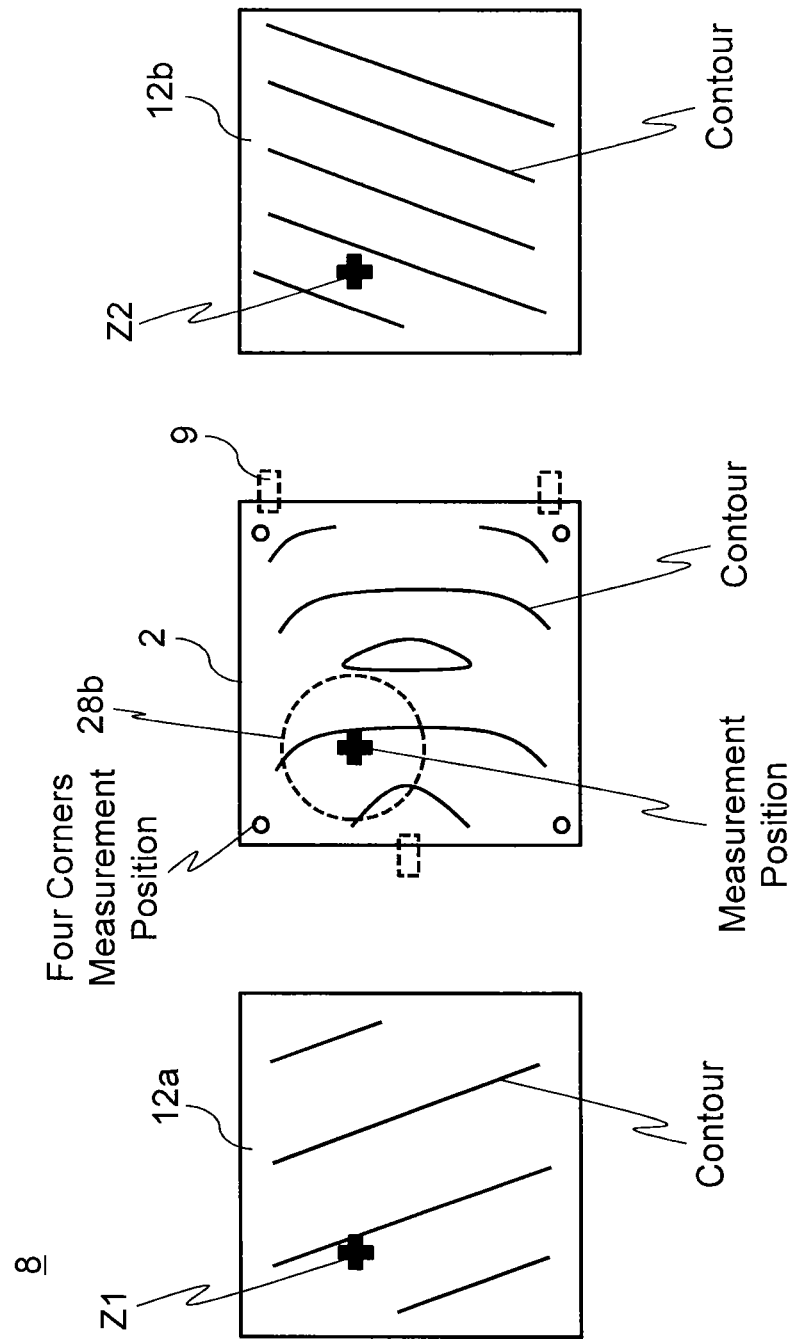
FIG. 7 is a view schematically illustrating a relationship between a first measuring surface including a first Z-sensor and a second measuring surface including a second Z-sensor with respect to the sample.

FIG. 7 is a view schematically illustrating a relationship between a first measuring surface including a first Z-sensor and a second measuring surface including a second Z-sensor with respect to the sample.

In FIG. 7, as described above, the Z-map is produced by measuring the height at the four corners (indicated as the four-corner measuring position in FIG. 7) of the sample 2 with respect to the center position of the objective lens in the sample 2, namely, the position in the height (Z) direction of the position where the inspection is performed (hereinafter, referred to as measuring position). Using the Z-map, the data of the target Z-height (Z-map target value) is obtained from the XY-position of the measuring position decided by the control of the Y-table 5 (not illustrated) and X-table 6 (not illustrated).

The Z-height at the measuring position of the sample 2 is calculated from a height Z1 at the position corresponding to the measuring position in the first measuring surface 12a and a height Z2 at the position corresponding to the measuring position in the second measuring surface 12b. The measuring position in the first measuring surface 12a is measured by the first Z-sensor 11a attached to the first measuring surface 12a, the measuring position in the second measuring surface 12b is measured by the second Z-sensor 11b attached to the second measuring surface 12b, and the first Z-sensor 11a and the second Z-sensor 11b are aligned along the same axis with respect to the measuring position. Specifically, the Z-height at the measuring position is expressed by $\{(Z1+Z2)2\}$. As described above, the Z-height data is used to correct the Z-map target value in the case that the position (Z-position) in the Z-direction (height direction) fluctuates (displacement in Z-direction) due to the mechanical factor when the sample 2 is moved in the X-direction or Y-direction (horizontal direction) during the inspection of the sample 2.

Figure 8:
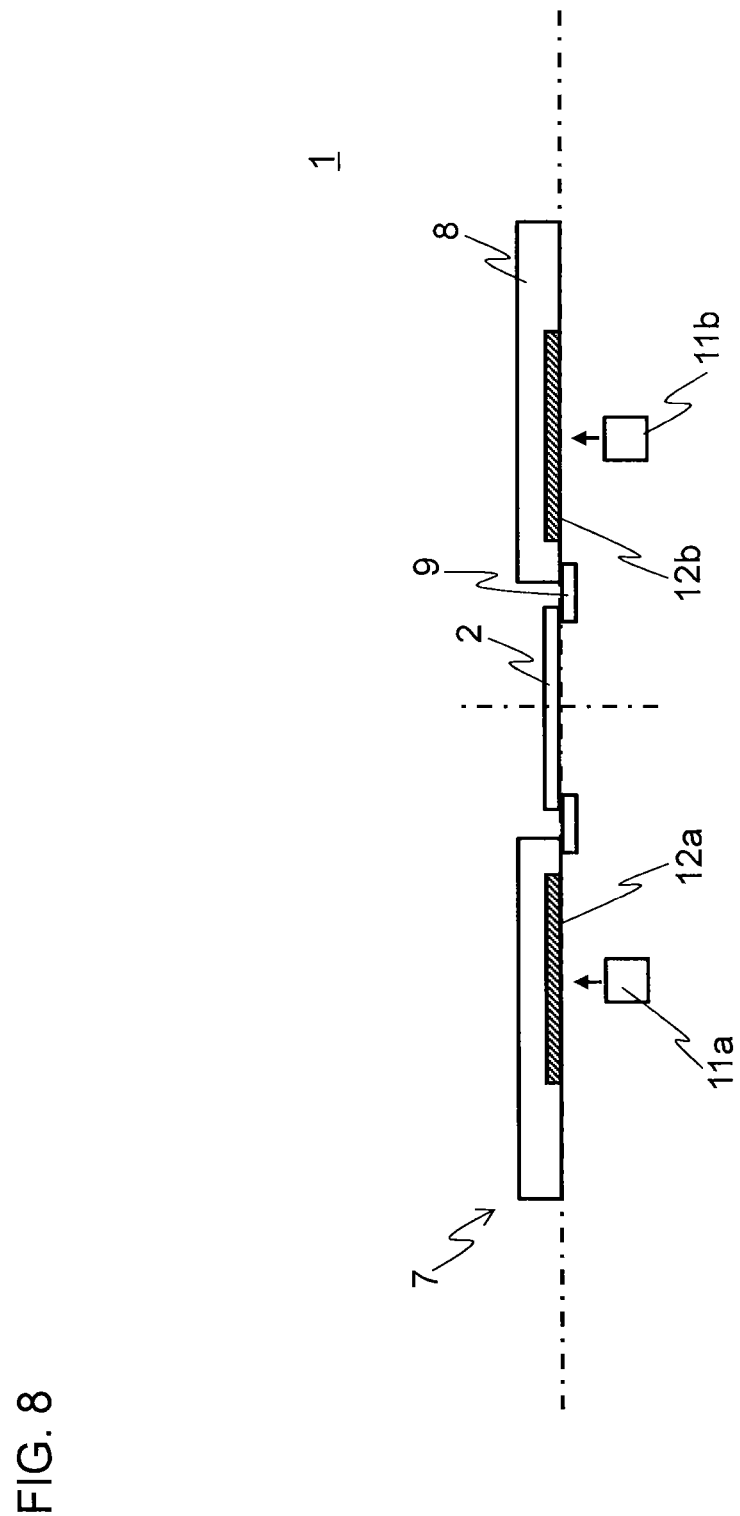
FIG. 8 is a sectional view schematically illustrating the sample and a main part configuration of the sample support apparatus of the embodiment.

FIG. 8 is a sectional view schematically illustrating the sample and a main part configuration of the sample support apparatus of the embodiment.

FIG. 8 illustrates the sample 2 and the main part configuration of the sample support apparatus 1 in FIG. 1. That is, the sample 2, the sample support 8 of Z-table 7 that supports the sample 2 using the support body 9, the first measuring surface 12a and second measuring surface 12b that are provided in the sample support 8, and the first Z-sensor 11a and second Z-sensor 11b that are provided according to the dispositions of the first measuring surface 12a and second measuring surface 12b are illustrated in FIG. 8. FIG. 8 illustrates the relationship among these components.

Figure 9:
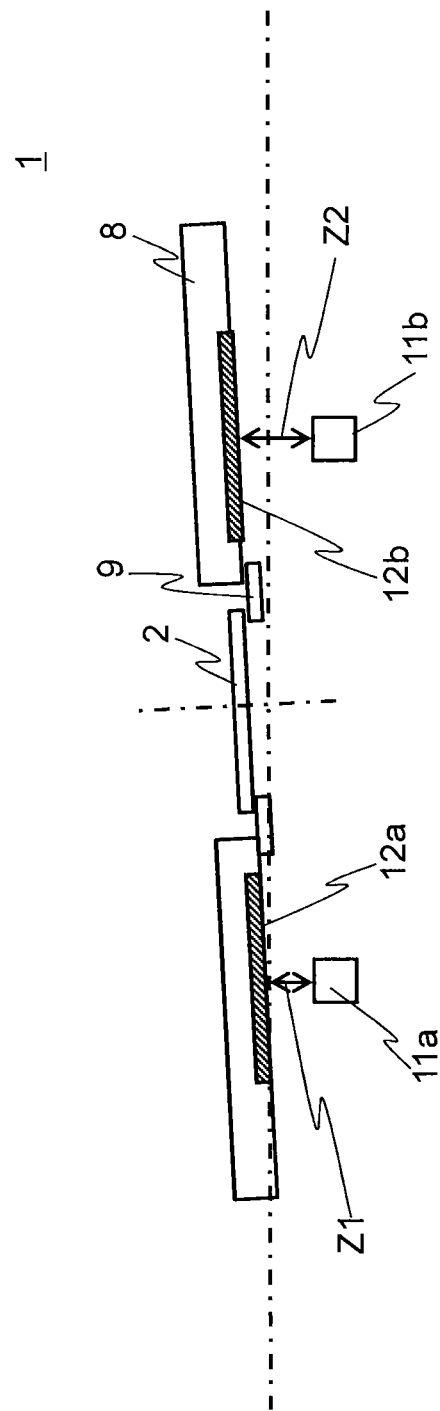
FIG. 9 is a view illustrating the displacement in the Z-direction and the correction at the Z-position using the first measuring surface and the second measuring surface.

FIG. 9 is a view illustrating the displacement in the Z-direction and the correction at the Z-position using the first measuring surface and the second measuring surface.

FIG. 9 illustrates the state, in the case that the displacement in the Z-direction is generated in the sample 2, the support body 9, the sample support 8, the first measuring surface 12a, the second measuring surface 12b, the first Z-sensor 11a, and the second Z-sensor 11b in FIG. 8.

For example, when the sample 2 is moved in the X-direction or Y-direction, the position (Z-position) in the Z-direction (height direction) fluctuates, namely, the displacement in the Z-direction is generated from the state in FIG. 8 due to the mechanical factor, sometimes the height of the second measuring surface 12b changes as illustrated in FIG. 9. Even if such a displacement in the Z-direction is generated, the Z-height at the measuring position of the sample 2 can be calculated from the height Z1 at the position corresponding to the measuring position in the first measuring surface 12a and the height Z2 at the position corresponding to the measuring position in the second measuring surface 12b. The measuring position in the first measuring surface 12a is measured by the first Z-sensor 11a attached to the first measuring surface 12a, the measuring position in the second measuring surface 12b is measured by the second Z-sensor 11b attached to the second measuring surface 12b, and the first Z-sensor 11a and the second Z-sensor 11b are aligned along the same axis with respect to the measuring position. That is, as described above, the Z-height at the measuring position can be obtained by calculating $\{(Z1+Z2)/2\}$.

At this point, as illustrated in FIG. 7, in the first measuring surface 12a and second measuring surface 12b on the sample support 8 of the Z-table 7 (not illustrated), sometimes a displacement in the Z-direction is generated in the measuring surface due to the accuracy, or lack thereof, of the measuring surface, the tilt during the attaching process, and the influence of the gravitational distortion. When the displacement in the Z-direction is measured in the range corresponding to the necessary inspection region in the measuring surface 12 using a blank reference with no pattern, the influence of the displacement in the Z-direction of the measuring surface 12 can be calculated with the previously measured displacement in the Z-direction used as the correction value. As to the measurement method, for example, reference data may be produced by measuring the measuring surface 12 a plurality of times with Z-sensor 11 values while the light is focused on the reference plate using a conventional optical autofocus (AF). At this point, when the influence of the gravitational distortion on the reference plate is removed, a Z-position correction table of the measuring surface 12 can be produced in the range corresponding to the necessary inspection region in the measuring surface 12 with respect to the virtual Z-reference surface in which the gravitational distortion is removed. Therefore, the height of the measuring surface 12 can be corrected.

Accordingly, the height Z1 of the first measuring surface 12a and the height Z2 of the second measuring surface 12b are corrected with the influence of the displacement in the Z-direction on the measuring surface 12 and the correction value (Z1 correction value and Z2 correction value), and as a result, the Z-height at the measuring position can be obtained with higher accuracy. Specifically, the Z-height at the measuring position can be expressed by $[\{Z1+Z1 \text{ correction value})+(Z2+Z2 \text{ correction value})\}/2]$. The correction amount at the Z-position can be calculated by subtracting the Z-map target value from $[\{(Z1+Z1 \text{ correction value})+(Z2+Z2 \text{ correction value})\}/2]$. Since actually the Z-measured value in the Z-measuring surface 12 has a given z-offset depending on the attaching position, it is necessary to have previously determined a Z-offset value.

As illustrated in FIG. 7, distortion is also generated in the sample 2. As described above, the influence of the gravitational distortion on the sample 2 is calculated by the well-known structural calculation. The Z-map target value at the measuring position is corrected as a Z-distortion correction value, and the Z-map target value can be obtained at a specific position with higher accuracy. In this case, in association with the height correction of the measuring surface, the correction amount can be expressed by "$[\{(Z1+Z1 \text{ correction value})+(Z2+Z2 \text{ correction value})\}/2]-Z$-map target value+Z-distortion correction value".

When an atmospheric pressure or temperature changes in the inspection in which the sample support apparatus 1 of the inspection apparatus is used, a focal position of the light with which the measuring position of the mesa portion 2a of the sample 2 is irradiated changes, and the height data of the surface of the sample 2 fluctuates as a result.

For example, a refractive index of air changes when the atmospheric pressure changes. Therefore, an imaging plane of an object, namely, the focal position, changes to generate focus displacement. For this reason, a focus displacement amount fluctuates by the change in atmospheric pressure, even if the Z-map is produced by the above method to even out the focus displacement amount by setting the height at the inspection position of the sample 2. It is necessary to correct the Z-map by measuring the amount of atmospheric pressure change to obtain the focus displacement amount.

It is known that a correlation exists between the change in atmospheric pressure and the change in focus displacement. Accordingly, the focus displacement amount can be predicted by measuring the change in atmospheric pressure. A barometer (not illustrated) is provided in the sample support apparatus 1, the height correction unit 10 processes a measurement result of the barometer as atmospheric pressure information, and the focus displacement amount is obtained from the atmospheric pressure information. Then, an atmospheric pressure correction amount is obtained using the focus displacement amount, the Z-map target value at the measuring position is corrected, and therefore the Z-map target value at the measuring position can be obtained with higher accuracy. In this case, in association with other correction values, the correction value can be expressed by "[{(Z1+Z1 correction value)+(Z2+Z2 correction value)}/2]−Z-map target value+Z-distortion correction value+atmospheric pressure correction amount".

As to the change in temperature, for example, when the temperature changes, the holding unit of the lens 28b that focuses the light from the second light source 29 on the four reference positions of the sample 2 expands or shrinks thermally, and the focal position changes to generate the focus displacement. The base 13 of the Z-sensor 11 expands or shrinks thermally, and the focal position changes to generate the focus displacement.

Therefore, the focus displacement amount fluctuates by the change in temperature, even if the Z-map is produced by the above method to set the height at the inspection position of the sample 2 to even out the focus displacement amount. At this point, a thermal expansion or shrinkage amount of the holding unit of the lens 28b or the base 13 of the Z-sensor 11 due to the temperature change is previously calculated from physical properties of a constituent material or actually measured, and data of a relationship between the temperature and the thermal expansion can be obtained.

The change in temperature is measured, the focus displacement amount is obtained by referring to the data previously of the change in dimension of the holding unit or the base 13 due to the thermal expansion, and the Z-map target value can be corrected.

Accordingly, the focus displacement amount can be predicted by measuring the change in temperature. A thermometer (not illustrated) is provided in the sample support apparatus 1, the height correction unit 10 processes the measurement result of the thermometer as temperature information, and the focus displacement amount is obtained from the temperature information. Then, a temperature correction amount is obtained using the focus displacement amount, the Z-map target value at the measuring position is corrected, and therefore the Z-map target value at the measuring position can be obtained with higher accuracy. In this case, in association with other correction values, the correction amount can be expressed by "[{(Z1+Z1 correction value)+(Z2+Z2 correction value)}/2]−Z-map target value+Z-distortion correction value+atmospheric pressure correction amount+temperature correction amount".

As described above, FIGS. 8 and 9 illustrate the adjustment of the height position of the sample 2. The height correction unit 10 of the sample support apparatus 1 controls the Z-table driving unit to adjust the height position of the sample 2.

Figure 10:
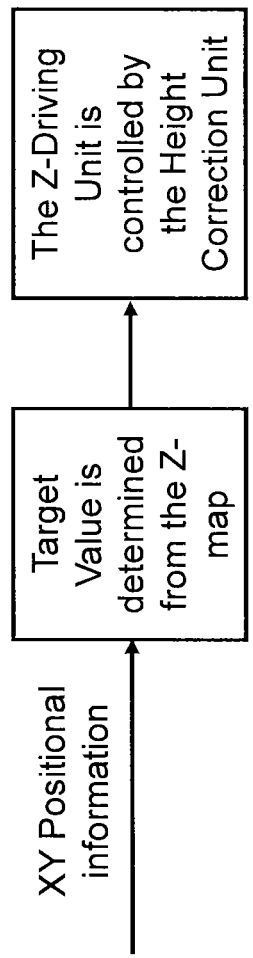
FIG. 10 is the block diagram illustrating the method for controlling the correction of the height (Z) of the sample using the non-corrected Z-map.
Figure 11:
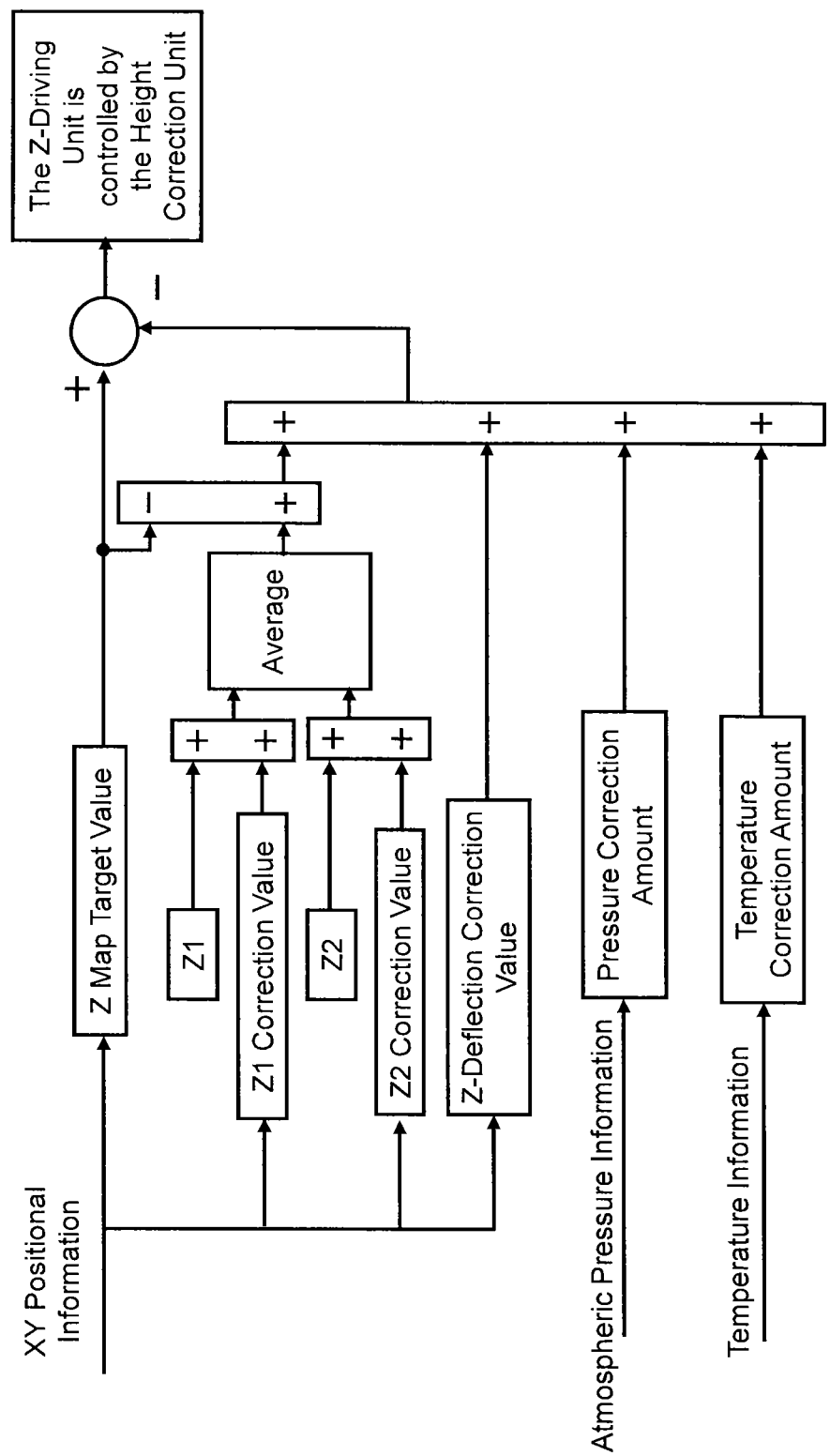
FIG. 11 is the block diagram illustrating the method for controlling the correction of the height (Z) of the sample using the corrected Z-map.

FIGS. 10 and 11 are block diagrams illustrating a method for controlling the correction of the height (Z) of the sample using the height correction unit of the sample support apparatus. FIG. 10 is the block diagram illustrating the method for controlling the correction of the height (Z) of the sample using the non-corrected Z-map. FIG. 11 is the block diagram illustrating the method for controlling the correction of the height (Z) of the sample using the corrected Z-map.

FIGS. 10 and 11 illustrate a function of the height correction unit 10 of the sample support apparatus 1, and illustrate the method in which the sample support apparatus 1 adjusts the sample 2 to the target height position.

The sample 2 is placed on the Z-table 7 as illustrated in FIG. 1. The Z-table 7 is movable in the horizontal direction by the Y-table 5 and the X-table 6. The movement positions of the Y-table 5 and X-table 6 are measured by the laser interferometer (not illustrated), and transmitted as XY-information data to the height correction unit 10.

As illustrated in FIG. 10, using the Z-map, the height correction unit 10 of the sample support apparatus 1 obtains the data of the target height (Z-map target value) at the measuring position that becomes the inspection position of the sample 2 from the XY-position information on the Y-table 5 and X-table 6. Based on the height data, the height correction unit 10 controls the Z-driving unit 15 of the Z-table 7 using the Z-height control unit 34, and adjusts the height of the sample 2 to the target height (Z-map target value).

In the case that the height (Z) position of the sample 2 is adjusted to the target position with higher accuracy, as illustrated in FIG. 11, the Z-map target value is corrected, and the Z-height of the sample 2 is adjusted based on the correction of the Z-map target value.

In this case, similarly to the case in FIG. 10, the sample 2 is placed on the Z-table 7 as illustrated in FIG. 1. The Z-table 7 is movable in the horizontal direction by the Y-table 5 and the X-table 6. The movement positions of the Y-table 5 and X-table 6 are measured by the laser interferometer (not illustrated), and transmitted as XY-information data to the height correction unit 10.

As illustrated in FIG. 11, using the Z-map, the height correction unit 10 of the sample support apparatus 1 obtains the data of the target height (Z-map target value) at the measuring position that becomes the inspection position of the sample 2 from the XY-position information on the Y-table 5 and X-table 6. The Z-map target value is then corrected.

That is, the correction is performed as one of the corrections using the measuring surface 12 in FIG. 1. The height (Z1) at the position corresponding to the measuring position, which becomes the measuring surface 12, in the first measuring surface 12a of the Z-table 7 and the correction value (Z1 correction value) in which the influence of the gravitational distortion on the first measuring surface 12a is calculated are added by an calculating unit (not illustrated) included in the height correction unit 10. Similarly, the height (Z2) at the position corresponding to the measuring position in the second measuring surface 12b of the Z-table 7 and the correction value (Z2 correction value) in which the influence of the gravitational distortion on the second measuring surface 12b is calculated are added. The calculating unit (not illustrated) of the height correction unit 10 calculates an average value (referred to as a correction value related to the measuring surface 12) of the correction value related to the first measuring surface 12a and the correction value related to the second measuring surface 12b, and the correction value related to the measuring surface 12 is the correction amount for the correction in which the measuring surface 12 is used.

As described above, the Z-distortion correction value in which the gravitational distortion of the sample 2 is considered is calculated as another correction.

As described above, the atmospheric pressure correction amount or the temperature correction amount is calculated as yet another correction.

The calculating unit (not illustrated) of the height correction unit 10 adds the amount of correction in which the measuring surface 12 is used, the Z-distortion correction value, the atmospheric pressure correction amount, and the temperature correction amount to calculate the correction data.

In the height correction unit 10, the calculating unit obtains the difference between the Z-map target value data at the measuring position of the sample 2 and the above correction data, and the corrected Z-map target value can then be obtained.

As illustrated in FIG. 11, based on the corrected Z-map target value, the height correction unit 10 controls the Z-driving unit 15 of the Z-table 7 using the Z-height control unit 34, and with great accuracy adjusts the height of the sample 2 to the target height. Therefore, in the inspection apparatus provided with the sample support apparatus 1, the inspection can be performed while the distance between the optical system 24 and the sample 2 is reliably kept constant.

As illustrated in FIG. 1, the optical image of the light, which is emitted from the first light source 25 and reflected by the sample 2, is formed on a photodiode array (for example, TDI sensor 43) disposed below the sample 2.

The pattern image formed on the photodiode array is subjected to photoelectric conversion by the photodiode array, and A/D (analog-to-digital) conversion by a sensor circuit (A/D circuit 44 in FIG. 1). An image sensor is disposed in the photodiode array. For example, a line sensor in which CCD cameras that are imaging elements arrayed in line is used as the image sensor. The TDI sensor 43 (Time Delay Integration Sensor) is one example of the line sensor. In the inspection apparatus, for example, the TDI sensor 43 captures the pattern image of the sample 2 while the X-table 6 in FIG. 1 continuously moves in the X-direction.

The optical image obtained by the inspection apparatus provided with the sample support apparatus 1 is transmitted to the defect detection circuit 45 of the sample support apparatus 1. More specifically, the optical image is transmitted to a comparison circuit constituting the defect detection circuit 45. Design pattern data of the sample 2 is also transmitted to the defect detection circuit 45 of the inspection apparatus. More specifically, the optical image is transmitted to the comparison circuit after the image is converted into reference image data by an expansion circuit and a reference circuit, which constitute the defect detection circuit 45.

In the comparison circuit, the optical image data transmitted from the sensor circuit (A/D circuit 44) and the reference image data generated by the reference circuit are compared to each other using a appropriate comparison determination algorithm, and a determination that the position is a defect is made when an error exceeds a predetermined value. Then, a coordinate of the defect and the optical image data and reference image data that become a basis for the defect determination are stored as an inspection result in a magnetic disk device included in the inspection apparatus. Thus, the inspection apparatus provided with the sample support apparatus 1 can inspect the inspection position of the sample 2 with high focus accuracy.

The present invention is not limited to the embodiments described and can be implemented in various ways without departing from the spirit of the invention.

The above description of the present embodiment has not specified apparatus constructions, control methods, etc. which are not essential to the description of the invention, since any suitable apparatus constructions, control methods, etc. can be employed to implement the invention. Further, the scope of this invention encompasses all support apparatuses employing the elements of the invention and variations thereof, which can be designed by those skilled in the art.

What is claimed is:

1. A sample support apparatus in which a XY-table and a Z-table moving along a height direction are disposed in a Z-reference surface as a height reference, and in which a sample is disposed at a predetermined height position while supported by the Z-table,
    the sample support apparatus comprising:
        a height correction unit that controls movement of the Z-table; and
        a Z-sensor that is provided on the Z-reference surface to measure the height from the Z-reference surface,
        wherein a measuring surface is aligned along the same axis with respect to a measuring position of the sample,
        the height of the measuring surface from the Z-reference surface is measured by the Z-sensor,
        the height correction unit moves the Z-table according to the measured value of the height so that the sample is disposed at the predetermined height position.

2. The sample support apparatus according to claim 1, wherein the measuring surface aligned along the same axis with respect to the measuring position of the sample comprises a first measuring surface and a second measuring surface, the measuring position of the sample being interposed between the first measuring surface and the second measuring surface,
    the Z-sensor includes a first Z-sensor and a second Z-sensor, the first Z-sensor and the second Z-sensor being provided on the Z-reference surface,
    the height of the first measuring surface from the Z-reference surface is measured by the first Z-sensor,
    the height of the second measuring surface is measured by the second Z-sensor,
    the height correction unit moves the Z-table according to each measured value of the height so that the sample is disposed at the predetermined height position.

3. The sample support apparatus according to claim 1, wherein the Z-table supports the sample at three points,
    the Z-table includes a measurement unit that sequentially irradiates at least four reference positions separated from one another on a measured sample surface with light, receives reflected light to sequentially measure the heights of at least the four reference positions, and produces a Z-map indicating a height distribution of the sample surface,
    the height correction unit moves the Z-table according to the measured value of the height by the Z-sensor and according to the Z-map by the measurement unit so that the
    the sample is disposed at the predetermined height position.

4. The sample support apparatus according to claim 3, wherein the height correction unit corrects the Z-map in consideration of gravitational distortion of the sample and a displacement in a height direction of the Z-table so that the sample is disposed at the predetermined height position.

5. The sample support apparatus according to claim 3, wherein the measurement unit includes a lens that sequentially focuses the light, a holding unit that holds the lens, and a base that is disposed on the Z-reference surface to support the Z-sensor thereon, and the height correction unit corrects the Z-map according to a displacement in focal position of the lens due to an influence of thermal expansion of the holding unit and a displacement in position of the Z-sensor due to the thermal expansion of the base so that the sample is disposed at the predetermined height position.

6. The sample support apparatus according to claim 4, wherein the measurement unit includes a lens that sequentially focuses the light, a holding unit that holds the lens, and a base that is disposed on the Z-reference surface to support the Z-sensor thereon, and the height correction unit corrects the Z-map according to a displacement in focal position of the lens due to an influence of thermal expansion of the holding unit and a displacement in installation position of the Z-sensor due to the thermal expansion of the base so that the sample is disposed at the predetermined height position.

7. The sample support apparatus according to claim 3, wherein the measurement unit includes a lens that focuses the light, and the height correction unit corrects the Z-map according to a displacement in focal position of the lens due to the influence of a change in refractive index of air caused by a change in atmospheric pressure so that the sample is disposed at the predetermined height position.

8. The sample support apparatus according to claim 4, wherein the measurement unit includes a lens that focuses the light, and the height correction unit corrects the Z-map according to a displacement in focal position of the lens due to the influence of a change in refractive index of air caused by a change in atmospheric pressure so that the sample is disposed at the predetermined height position.

9. The sample support apparatus according to claim 5, wherein the height correction unit corrects the Z-map according to a displacement in focal position of the lens due to the influence of a change in refractive index of air caused by a change in atmospheric pressure so that the sample is disposed at the predetermined height position.

10. The sample support apparatus according to claim 1, wherein the Z-sensor is at least one of an electrostatic capacitance sensor, an electromagnetic induction sensor, and an optical sensor.

* * * * *